United States Patent
Drevillon et al.

(10) Patent No.: US 6,868,312 B2
(45) Date of Patent: Mar. 15, 2005

(54) METHOD FOR REAL-TIME CONTROL OF THE FABRICATION OF A THIN-FILM STRUCTURE BY ELLIPSOMETRIC MEASUREMENT

(75) Inventors: Bernard Drevillon, Clamart (FR); Thibaut Heitz, Fontenay-aux-Roses (FR); Jean-Christophe Rostaing, Buc (FR)

(73) Assignee: L'Air Liquide Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 198 days.

(21) Appl. No.: 09/921,786

(22) Filed: Aug. 6, 2001

(65) Prior Publication Data
US 2002/0126283 A1 Sep. 12, 2002

(30) Foreign Application Priority Data
Aug. 10, 2000 (FR) .......................................... 00 10532

(51) Int. Cl.$^7$ .............................................. H01H 43/00
(52) U.S. Cl. ........................... 700/306; 700/28; 700/46; 700/121; 356/369
(58) Field of Search ........................... 700/28, 46, 121, 700/306; 356/369, 72; 760/296; 438/16; 427/10

(56) References Cited

U.S. PATENT DOCUMENTS

| | | | | |
|---|---|---|---|---|
| 5,042,951 A | * | 8/1991 | Gold et al. ................. | 356/369 |
| 5,223,356 A | * | 6/1993 | Kumar et al. ................. | 430/1 |
| 5,494,697 A | * | 2/1996 | Blayo et al. ................. | 427/10 |
| 6,081,334 A | * | 6/2000 | Grimbergen et al. ....... | 356/499 |
| 6,504,608 B2 | * | 1/2003 | Hallmeyer et al. ......... | 356/369 |
| 2002/0024668 A1 | * | 2/2002 | Stehle et al. ................ | 356/369 |

FOREIGN PATENT DOCUMENTS

EP 0653621 A1 * 5/1995 .......... G01N/21/21

OTHER PUBLICATIONS

Kildemo et al., "Real time control of the growth of silicon alloy multilayers by multiwavelength ellipsometry"; Thin Solid Films, Dec. 1996; vol. 290–291; pp. 46–50.*
M. Kildemo et al., "A direct robust feedback method for growth control of optical coatings by multiwavelength ellipsometry"; Thin Solid Films, Dec. 1998; vol. 313–314; pp. 484–489.*
Kildemo et al, "A direct robust feedback method for growth control of optical coatings by multiwavelength ellipsometry"; *Thin Solid Films*, vol. 313–314; Feb. 1998; pp. 484–489.
Kildemo et al, "Real time control of the growth of silicon alloy multilayers by multiwavelength ellipsometry"; *Thin Solid Films*; vol. 290–291; Dec. 1996; pp. 46–50.
Brevillon, "Phase modulated Ellipsometry From the Ultraviolet to the Infrared: In Situ Application to the Growth of Semiconductors"; *Progress in Crystal Growth and Characterization of Materials*; vol. 27, No. 1 (1993); pp. 1–87.
Search Report issued in French Application No. 00 10532.

* cited by examiner

*Primary Examiner*—Leo Picard
*Assistant Examiner*—Carlos Ortiz Rodriguez
(74) *Attorney, Agent, or Firm*—Burns, Doane, Swecker & Mathis, L.L.P.

(57) ABSTRACT

Method for real-time control of the fabrication of a thin-film structure comprising a substrate by ellipsometric measurement in which:

variables directly linked to the ellipsometric ratio $\rho = \tan\Psi \exp(i\Delta)$ are measured; and the said variables are compared with reference values. The comparison relates to the length of the path traveled at a time t in the plane of the variables with respect to an initial point at time $t_0$, for each layer participating in the thin-film structure.

33 Claims, 3 Drawing Sheets

METHOD FOR REAL-TIME CONTROL OF THE FABRICATION OF A THIN-FILM STRUCTURE BY ELLIPSOMETRIC MEASUREMENT

BACKGROUND OF THE INVENTION

1. Field of the Invention

The present invention relates to a method for real-time control of the fabrication of a thin-film structure by ellipsometric measurement.

2. Description of the Related Art

Ellipsometry is a non-destructive measurement technique for optically characterizing a specimen having a specular or quasi-specular surface.

Ellipsometry can be used in situ and therefore makes it possible to study the mechanisms involved in the growth of thin layers and in the formation of interfaces and to control the process for fabricating these layers and interfaces. Ellipsometry is, for example, used to study and control the fabrication of semiconductor materials and components.

Ellipsometric measurements may be carried out at a fixed wavelength or at several wavelengths (spectroscopic ellipsometry). Depending on the wavelength range of the optical components used (source, detector, etc.), it is possible to obtain different properties of the layers and of the materials or to explore different materials.

In the ultraviolet and visible range, the depth of penetration of the radiation is quite small. This constitutes favorable conditions for the study of surfaces and interfaces, and for real-time control. But this does not always allow volume properties of the layers and the materials to be obtained, properties which then have to be determined by measurements in the near-infrared range.

The far infrared is well suited to vibrational absorption measurements (chemical bonds).

In order to make ellipsometric measurements, the surface of a specimen is illuminated with a light beam and the state of polarization of an incident beam i is compared with that of the reflected beam r or transmitted beam. The polarization vector E is generally represented by its projections $E_s$ and $E_p$ perpendicular and parallel to the plane of incidence, respectively. The projections $E_p$ and $E_s$ are complex quantities.

In the field of ellipsometry, the ratio $\rho=(E_p/E_s)^r/(E_p/E_s)^i$, signifying modifications in the state of polarization which are produced by the surface studied, is generally represented in the form:

$$\rho=\tan\Psi \cdot \exp(i\Delta)=(E_p/E_s)^r/(E_p/E_s)^i$$

The two angles $\Psi$ and $\Delta$ describing the change in polarization are thus combined in the complex quantity $\rho$.

The angles $\Psi$ and $\Delta$, and therefore $\rho$, depend on the properties of the specimen as well as on the angle of incidence of the beam and the measurement wavelength. The expression for $\Psi$ and $\Delta$ or for $\rho$, as a function of these parameters, is given by the Fresnel equations quoted, for example, by D. Charlot and A. Maruani in Appl. Opt. 24, 3368, 1985.

In phase-modulated ellipsometry, an incident ray has its polarization modulated by a phase difference generated between two specific axes of a phase modulator. The phase shift $\delta(t)$ typically changes with time t in a periodic angular frequency $\omega$ law, $\delta(t)$ being proportional to the first order to $\sin(\omega t)$.

In phase-modulated ellipsometry, the intensity of the light flux reflected by a specimen is used to deduce, in a known manner, the values of $\Psi$ and $\Delta$.

Ellipsometry, and more particularly phase-modulated spectroscopic ellipsometry (PMSE), is a powerful technique for measuring, in real time, the growth of layers on a substrate. This technique has the advantage of not disturbing the process being carried out. Moreover, it is very sensitive to physical parameters of the specimen measured, such as the thickness d of the layer and the refractive index n. Furthermore, it allows rapid measurements (Bernard Drevillon, "*Progress in crystal growth on characterisation of material*", vol. 27, 1998, p. 1–87).

According to a known method, the angles $\Psi$ and $\Delta$, or $\rho$, are calculated from amplitude measurements. These quantities $\Psi$ and $\Delta$ depend on physical parameters of the specimen measured, such as the index n and the thickness d of the surface layer. In the case of transparent materials, these parameters may thus be calculated from $\Psi$ and $\Delta$ by direct inversion of the Fresnel equations. This inversion must in general be carried out iteratively.

The application of phase-modulated spectroscopic ellipsometry to in situ growth control is, for example, described in the document "*High-speed spectral ellipsometry for in situ diagnostics and process control*", Duncan et al., J. Vac. Sci. Technol. B., 12(4), 1994.

It is in fact often difficult to deposit a structure consisting of several layers of different thickness and refractive index, for example by PECVD (Plasma Enhanced Chemical Vapor Deposition) in order to obtain the necessary accuracy (about 2%) required for the production of optical filters for example. It is insufficient to choose the deposition times for each layer from the growth rates of these layers measured during previous experiments. Real-time control, with a feedback loop on the deposition parameters therefore becomes indispensable.

Various approaches have already been followed in order to improve these ellipsometric measurement methods and to apply them to such industrial processes.

In particular, patent FR-2,731,074 proposes to estimate, during a process for fabricating layers, the physical parameters of the said layers from measurements made by ellipsometry and to approximate them using the method of adjustment by the method of least squares of theoretical values taken as reference.

More particularly, these methods generally require intermediate calculations to be carried out on the basis of raw measurements (such as interferential calculations taking into account the totality of the layer deposited), thereby considerably slowing down their implementation.

Another method has also been proposed (M. Kildemo, P. Bulkin, S. Deniau and B. Drevillon, Appl. Phys. Lett. 68, 1996, p. 3395). This consists in measuring, in real time, in the $(I_s,I_c)$ plane, where $I_s$ and $I_c$ are known functions which will be explained later, the distance between the measured point and the theoretical point corresponding to the end of each sublayer.

This method requires a very precise knowledge of each path end. It therefore has the drawback of being very sensitive to systematic errors, especially in the applications involving multiple wavelengths. These systematic errors (such as those due to ellipsometry calibration errors) will tend to artificially make the experimental path depart from the theoretical path. This may considerably reduce the precision of the control.

It also requires precise optical knowledge about the substrate, this often being difficult in the case of heterogeneous materials or materials which are not very absorbent, such as the standard glasses.

These various methods therefore each have drawbacks— they are either slow or lack precision.

SUMMARY OF THE INVENTION

It is an object of the present invention to remedy these drawbacks by providing a method for real-time control of the fabrication of thin-film structres by ellipsometric measurement which makes use of the temporal variations in the raw ellipsometric measurement, that is to say without having to have recourse to the optical inversions or parameterizations needed to obtain the optical parameters from $\Psi$ and $\Delta$.

For this purpose, the invention relates to a method for real-time control of the fabrication of a thin-film structure by ellipsometric measurement in which:

variables directly linked to the ellipsometric ratio $\rho = \tan \Psi \exp(i\Delta)$ are measured; and the said variables are compared with reference values.

According to the invention, the comparison relates to the length of the path traveled at a time t in the plane of the variables with respect to an initial point at time $t_0$, for each layer participating in the thin-film structure.

Variables directly linked to the ellipsometric ratio $\rho$ are understood to mean here variables which are directly obtainable from the signal delivered by the ellipsometer detector without it being necessary to use laborious mathematical treatments such as equation inversions and adjustments using the method of least squares.

The parameter taken into consideration for controlling the fabrication of thin-film structres is, for each layer, the length of the path at a time t which will be controlled by acting on the parameters for fabricating the layers.

The present invention also relates to the characteristics which will become apparent from the following description and which should be considered separately or in any technically possible combination:

the said variables are a combination of the parameters $\Psi$ and $\Delta$;

the said variables are a combination of trigonometric functions of the parameters $\Psi$ and $\Delta$;

the ellipsometric measurement is one with phase modulation.

Phase-modulated ellipsometry is understood to mean measurement obtained by an ellipsometer which includes a photoelastic or electrooptic modulator placed after an entrance polarizer. The measurement is obtained by using the signal delivered by a photodetector placed at the exit, after the excitation light signal has been reflected off the specimen and passed through an analyzer.

Since the symmetrical operation of these devices is well known, the photoelastic modulator may possibly be placed on the light beam after reflection off the specimen;

the measured variables are, respectively:

$I_s = (\sin 2\Psi \sin \Delta)$ and $I_c = (\sin 2\Psi \cos \Delta)$ or $I_c = \cos 2\Psi$;

the ellipsometric measurement is made using the method called "rotating polarizer" method.

Ellipsometric measurement made using the method called "rotating polarizer" method is understood to mean the measurements obtained by the use of an ellipsometer which includes a rotating polarizer, the measurement resulting from the signal delivered by the photoreceptor after reflection off the specimen and passage through an analyzer.

Here again, it is known that the operation of such an ellipsometer is symmetrical and that the entrance polarizer may be stationary, the analyzer being given a rotational movement.

In any type of ellipsometer, a compensator may be inserted in one of the arms. It is also possible to use a rotating compensator to make the modulation;

the measured variables are $\tan \Psi$ and $\cos \Delta$;

the ellipsometric measurement is a multiwavelength measurement.

The multiwavelength measurement is that obtained by spectroscopic ellipsometers which differ from monochromatic ellipsometers in which the excitation light has a very limited spectrum around a given wavelength;

the reference values are a theoretically determined path;

the reference values are an experimentally determined path;

the reference values are discrete points corresponding to instants in the fabrication of the thin layers with respect to the time $t_0$–$t_0$ may correspond to the start of deposition on the substrate or the start of growth of one of the constituent layers of the structure;

the path traveled is adjusted by a polynomial of order between 1 and 5;

the reference values are determined by measurement, using the succession of the following steps:

measurement of a known layer on a simple substrate;

measurement of the same known layer on an industrial substrate;

measurement of the thin-film structre to be controlled.

BRIEF DESCRIPTION OF THE FIGURES OF THE DRAWINGS

The invention will be described hereinbelow in greater detail with reference to the appended drawings in which.

DETAILED DESCRIPTION OF THE PREFERRED EMBODIMENTS

Figure 1:
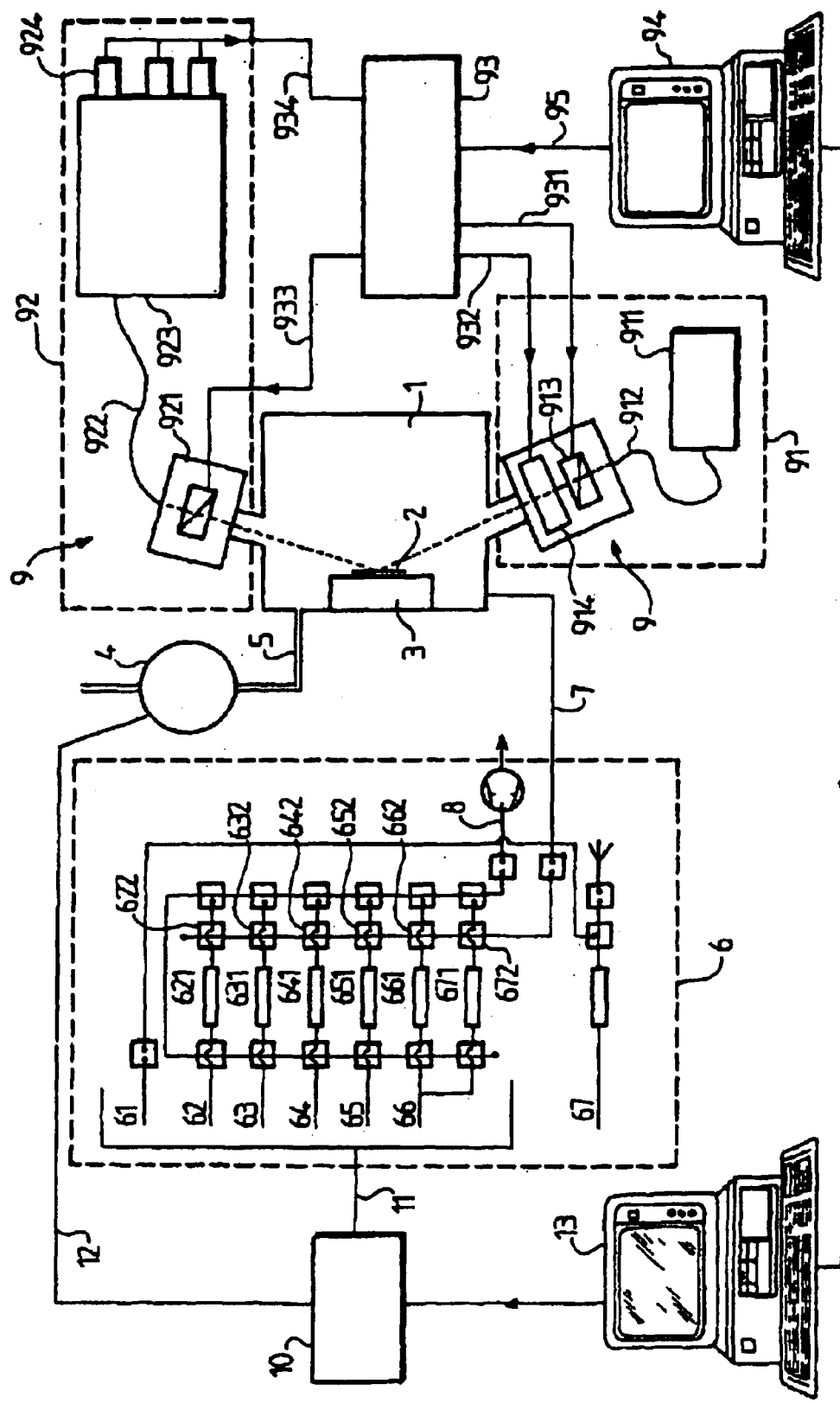
FIG. 1 is a simplified representation of a manufacturing plant using the invention.

The fabrication processes intended here are essentially plasma deposition of thin layers and of multilayer structures or layers with composition gradients (optical filters), or the plasma etching of microelectronic components. More generally, the control method proposed, principally applied to PECVD (Plasma Enchanced Chemical Vapor Deposition) processes, can be applied to other fabrication processes using gases or organometallic compounds (CVD: Chemical Vapour Deposition and MOCVD: Metal Organic Chemical Vapour Deposition) or may be generalized to processes based on the use of solid sources or targets (sputtering, vacuum evaporation, molecular beam epitaxy, etc.). In the latter case, the feedback on the basis of ellipsometric measurements is not effected on gas management but on other control parameters (currents, temperature, etc.).

The fabrication plant comprises a plasma chamber 1 in which the substrate 2 is placed, this substrate being, for example, the starting component of the semiconductor wafer to be fabricated. This substrate is fixed to a support 3. The reduced pressure in the plasma chamber 1 is obtained by the action of the pump 4 connected to the plasma chamber via the line 5. The gas panel 6 feeds the plasma chamber 1 via the line 7 and is connected to gas supplies, a nitrogen $N_2$ supply 61, an ammonia $NH_3$ supply 62, a hydrogen $H_2$ supply 63, a methane $CH_4$ supply 64, a helium He supply 65, a silane $SiH_4$ supply 66 and an oxygen $O_2$ or nitrous oxide $N_2O$ supply 67, respectively.

The inlets 62 to 65 are each connected to the line 7 via a flowmeter 621, 631, 641, 651 and a valve 622, 632, 642, 652.

The silane supply 66 is connected to two flowmeters 661 and 671 and two valves 662 and 672.

Conventional draining and purging means 8, especially a vacuum pump, ensure that the gas panel is operated conveniently and safely.

The growth of the layers on the substrate 2 in the plasma chamber 1 is controlled using an ellipsometer 9 consisting of an emission head 91 and a receiver unit 92.

The emission head 91 comprises a multiwavelength source 911 connected via an optical fiber 912 to a unit consisting of a polarizer 913 and a phase modulator 914.

An example of a spectroscopic ellipsometer is described in the European Patent EP 0 663 590.

The receiver unit 92 comprises a polarizer-analyzer 921 connected via an optical fiber 922 to a spectrograph 923 followed by an array of photodetectors 924.

The ellipsometer 9 is controlled by a processing unit 93 controlled by a computer 94.

The processing unit 93 controls the polarizer 913 and the modulator 914, via the electrical links 931 and 932 respectively, and receives the signal from the multiwavelength detector 924 via the electrical link 934. Its link to the computer 94 is provided by the electrical connection 95.

The gas panel 6 is controlled by a processing unit 10 to which it is connected by the connections 11. This processing unit 10 also controls, via the link 12, the pump 4 and/or the power of the plasma generator and is controlled by a microcomputer 13 which is itself connected to the microcomputer 94 via a link 14.

Thus, the ellipsometer 9 makes it possible to obtain, by means of the processing unit 93 and the microcomputer 94, the physical and chemical characteristics of the layer being deposited on the substrate 2. This information is compared with the characteristics of the product to be fabricated (and possibly their variations over time) which have been stored beforehand in the memory of the computer 94.

The result of this comparison controls, via the connection 14, the instructions delivered by the computer 13 to the processing unit 10 which determines the nature and the concentration of the gases injected via the control panel 6 into the plasma chamber 2.

Thus, the fabrication process is completely controlled and the products thus fabricated are optimized.

The processing unit 93 and the computer 94 are programmed in such a way that the properties of the layer deposited on the specimen 2 can be controlled by a small number of predetermined parameters.

In this embodiment, the variables directly linked to the ellipsometric ratio generated by a spectroscopic ellipsometer during the fabrication of thin layers, or more precisely a thin-film structure, are monitored in real time. This thin-film structure may consist of a single layer or of several layers (for example in the case of optical filters).

The method of the invention is also suitable for graded-index thin-film structures which may be decomposed into a stack of elementary layers having a fixed composition.

Using an ellipsometric method offers many advantages and allows rapid data acquisition without disturbing the fabrication process. Compared with conventional reflectometry measurements, it has the advantage of higher sensitivity associated with the simultaneous determination, at each wavelength, of two quantities instead of only one.

The variables used are directly linked to the usual ellipsometric ratio $\rho = \tan \Psi \exp(i\Delta)$, where $\rho = r_p/r_s$, $r_p$ and $r_s$ being the reflection coefficients of the light polarized parallel and perpendicular to the plane of incidence, respectively.

Within the context of phase-modulated ellipsometry, the sensor enables the quantities $I_s=(\sin 2\Psi \sin \Delta)$ and $I_c=(\sin 2\Psi \cos \Delta)$ or, equivalently, $I_c=(\sin 2\Psi \cos 2\Psi)$ or $I_c=\cos 2\Psi$ to be obtained directly.

It is therefore these two parameters $I_s=(\sin 2\Psi \sin \Delta)$ and $I_c=(\sin 2\Psi \cos \Delta)$ or $I_c=\cos 2\Psi$ which are used in this particular case for implementing the control method of the invention.

In the case of an ellipsometer with a rotating polarizer, the ellipsometric parameters that can be obtained directly are $\tan \Psi$ and $\cos \Delta$.

It is essential to use parameters which can be obtained without complex calculations, that is to say calculations which require computer processing taking time, such as for example the multilayer interferometric calculation, the adjustment by the method of least squares, etc., and therefore not easily compatible in order to ensure optimum precision when controlling a process in real time.

It therefore goes without saying that any combination of the trigonometric functions of $\Psi$ and $\Delta$ directly obtainable by measurement may also be used to carry out this control.

Figure 2:
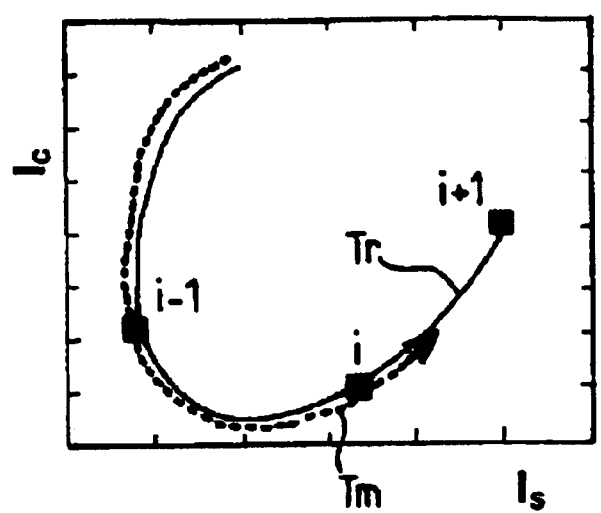
FIG. 2 is a schematic representation, in the $I_s, I_c$ plane, of an experimental path with respect to a theoretical path under a simplified assumption, the structure being made up of various layers i–1, i, i+1.
Figure 3:
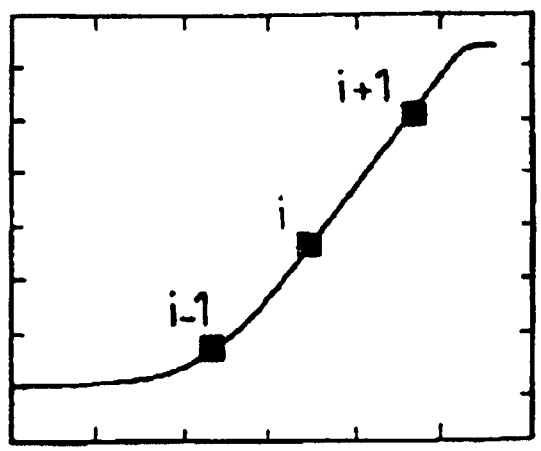
FIG. 3 is the schematic representation of the length of the path for a thin-film structure as a function of time.

As shown in FIG. 2, the method consists in comparing, in real time, the length of the measured path $T_m$ in the $(I_s, I_c)$ plane with respect to the expected length of a reference path $T_r$.

This comparison may be made for the entire layer if it is uniform or for each of the layers making up the structure.

It is thus possible to control the end of each layer or sublayer and to initiate the deposition of the next layer.

The use of a spectroscopic multiwavelength ellipsometer, in real time, makes it possible to improve the precision of the process although this is not necessary. This is because it is possible, provided that there is no need for optimum precision, to use the method of the invention with a single-wavelength ellipsometer.

In practice, the ellipsometric measurement of the initial point is firstly made at the start of fabrication of the thin-film structre, the reference path $T_r$ being calculated using this initial measurement. To eliminate the influence of the experimental noise during real-time comparison, the measurements of $I_s$ and $I_c$ as a function of time are advantageously adjusted by a polynomial, for example a second-order polynomial, over a window of variable width typically corresponding to about ten nanometers.

With a multiwavelength ellipsometer, the sum of the measured differences is calculated at each wavelength from the reference and experimental lengths. When this difference changes sign, deposition of the next layer is initiated.

Since the measurements are always affected by insignificant rapid fluctuations, adjustment by a polynomial consists in smoothing the measured curve by replacing it with the closest curve, within a given time window, represented by a polynomial of fixed order, generally between 1 and 5, and preferably of the second order.

This method is very general, it can be applied to transparent thin-film structures deposited on any substrate (whether transparent or absorbent) and it applies whatever the thickness of the structure. It may also be extended to the case of layers which are not very absorbent, or even to the direct characterizing of a substrate.

In certain cases, in particular when it is desired to deposit layers on a complex, transparent and inhomogeneous substrate (such as standard glass), it may prove difficult to determine the reference path.

The method is then carried out in the following manner:

firstly, a known layer is deposited on a substrate, called a simple substrate, allowing controlled ellipsometric measurements of the said layer. Such a substrate is either an opaque substrate, for example made of single-crystal silicon, or a homogeneous transparent or partially transparent substrate, that is to say, for example, fused silica or a borosilicate glass (Corning 7059, for example).

Thus, a number of ellipsometric measurements is made allowing the layer and its substrate to be fully characterized. For this purpose, a conventional ellipsometric measurement is firstly made on the substrate and then, during deposition of the transparent layer, the parameters $I_s, I_c$ are measured and, in general for several wavelengths, a set of curves representing the variations in the parameters $I_s, I_c$ for each wavelength, as a function of time is obtained. This allows the rate of deposition and the refractive index of the layer for each wavelength to be calculated. These values will consequently be used to describe the growth of this layer;

in a second step, the same layer is deposited, that is to say using the same gases with the same process as in the previous step, on the complex substrate called the industrial substrate which it will be desired to use in the industrial process.

Here again, the variations in the parameters $I_s, I_c$ for various wavelengths, over time during the deposition, and more particularly the length $L_2(I_s, I_c)$ (t), are recorded.

From this are then calculated, for example by an adjustment using the method of least squares based on the lengths $L_2(I_s, I_c)$ (t), the effective index n and the effective absorption coefficient k of the substrate for each wavelength.

The precision can be improved by using dispersion relationships which give the variations $n(\lambda)$ and $k(\lambda)$ of the substrate. It is also possible to use reflection and transmission measurements, at normal incidence, to characterize the industrial substrate and the layer;

in a third step, knowing the effective n, k parameters of the substrate for the various wavelengths of the substrate, it is possible to calculate the theoretical curve $L_3(I_s, I_c)$ (t) for a particular layer structure deposited during the industrial process, using the method of the invention.

FIG. 2 shows schematically a measured path $T_m$ with respect to a theoretical or reference path $T_r$. The figure shows the deposition of a layer i of the structure between the layer i–1 and the layer i+1. According to the invention, for each layer i, the curvilinear length of the layer $T_m$ is compared with that of the curve $T_r$ between the point i–1 and the point i.

Figure 4:
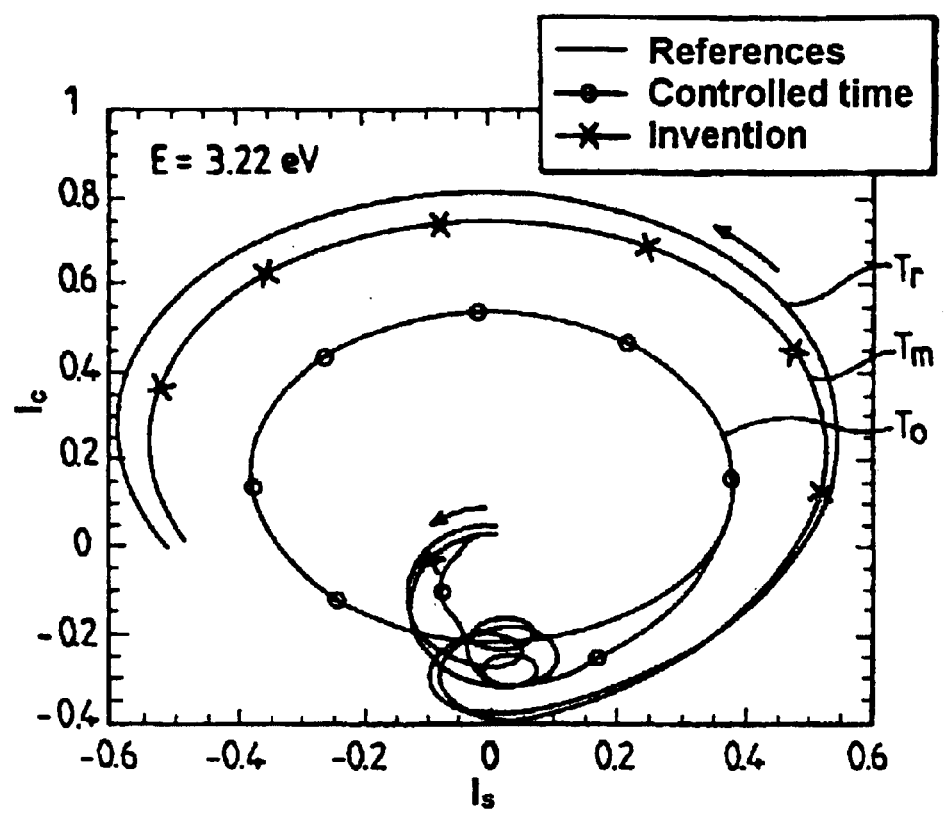
FIG. 4 is the representation of an actual path, in the $I_s, I_c$ plane, corresponding to a wavelength, for the deposition of an antireflection filter on Corning 7059 glass.

FIG. 4 is the result of an actual experiment. The reference curve is denoted by $T_r$. The measured curve, according to the invention, as indicated above, is denoted by $T_m$ (with the "x" symbols). The curve denoted by $T_o$ (with the "o" symbols) is the result of the ellipsometric measurements made on the same multilayer structure, the layers being deposited, not according to the invention but according to a conventional process by applying a method in which the deposition time for each layer is controlled with respect to a predetermined reference time. It should be noted that the curve $T_o$ rapidly departs from the theoretical reference curve $T_r$, whereas curves $T_m$ and $T_r$ are close together. The path in FIG. 4 corresponds to the deposition of an antireflection filter on a glass substrate.

Figure 5:
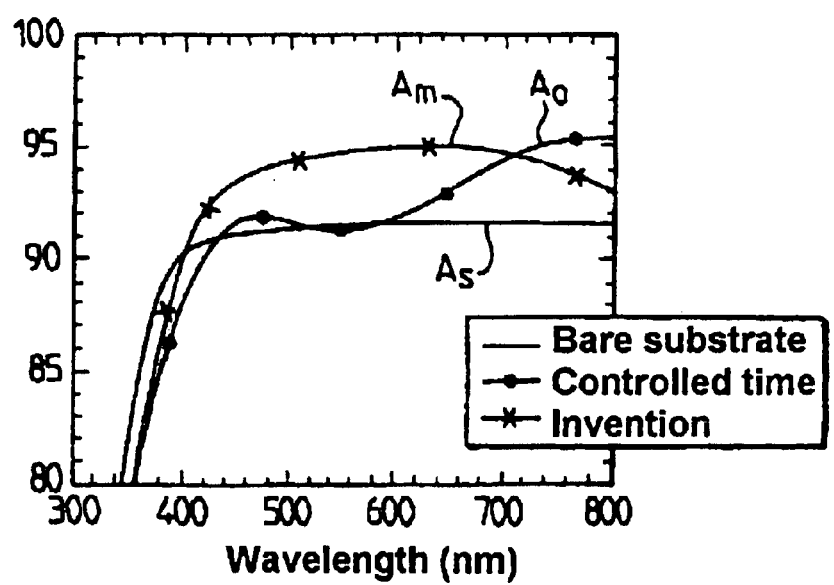
FIG. 5 represents the compared characterization, by spectrophotometry, of the filter forming the subject of FIG. 4.

FIG. 5 is also indicative of the result obtained. The properties of the multilayer structure finally produced were measured by spectrophotometry:

$A_s$ denotes the curve for the bare substrate;

$A_m$ denotes the curve for the structure obtained according to the invention, corresponding to the curve $T_m$ in FIG. 4;

$A_o$ denotes the curve for the structure obtained according to the prior art, corresponding to the curve $T_o$ in FIG. 4.

It may be seen that the use of the invention considerably reduces the reflection coefficient of the substrate, this not being the case according to the prior art.

What is claimed is:

1. A method for real-time control of the fabrication of a thin-film structure by ellipsometric measurement, said method comprising:

(a) reflecting a polarized beam of light from a surface of said structure;

(b) measuring real-time control variables representative of the reflected beam, said variables directly linked to an ellipsometric ratio $\rho = \tan \Psi \exp (i\Delta)$;

(c) providing reference values to form a theoretical or experimental path; and (d) comparing a path traveled by said reflected beam with the reference values, wherein the said comparison involves the length of the path traveled by said polarized beam of light at a time t in a plane of the variables with respect to an initial point at time to for each layer in the thin-film structure.

2. Control method according to claim 1, wherein the said variables are a combination of the parameters $\Psi$ and $\Delta$.

3. Control method according to claim 2, wherein the ellipsometric measurement is one with phase modulation.

4. A method according to claim 3, wherein the measured control variables are, respectively:

$I_s = (\sin 2\Psi \sin \Delta)$ and $I_c = (\sin 2\Psi \cos \Delta)$ or $I_c = \cos 2\Psi$.

5. Control method according to claim 2, wherein the ellipsometric measurement is carried out using the "rotating polarizer" method.

6. Control method according to claim 5, wherein the measured variables are $\tan \Psi$ and $\cos \Delta$.

7. Control method according to claim 2, wherein the ellipsometric measurement is a multiwavelength measurement.

8. Control method according to claim 2, wherein the reference values from a theoretically determined path.

9. Control method according to claim 2, wherein the reference values form an experimentally determined path.

10. Control method according to claim 2, wherein the reference values are discrete points corresponding to the instants of fabrication of the thin layers with respect to the time $t_0$.

11. Control method according to claim 2, wherein the path traveled is adjusted by a polynomial of order between 1 and 5.

12. Control method according to claim 2, wherein the reference values are determined by measurement, using the succession of the following steps:

measurement of a known layer on a simple substrate;

measurement of the same known layer on an industrial substrate;

measurement of the thin-film structure to be controlled.

13. Control method according to claim 1, wherein the said variables are a combination of trigonometric functions of the parameters $\Psi$ and $\Delta$.

14. Control method according to claim 13, wherein the ellipsometric measurement is one with phase modulation.

15. A method according to claim 14, wherein the measured control variables are, respectively $I_s = (\sin 2\Psi \sin \Delta)$ and $I_c = (\sin 2\Psi \cos \Delta)$ or $I_c = \cos 2\Psi$.

16. Control method according to claim 13, wherein the ellipsometric measurement is carried out using the "rotating polarizer" method.

17. Control method according to claim 16, wherein the measured variables are tan $\Psi$ and cos $\Delta$.

18. Control method according to claim 13, wherein the ellipsometric measurement is a multiwavelength measurement.

19. Control method according to claim 13, wherein the reference values form a theoretically determined path.

20. Control method according to claim 13, wherein the reference values form an experimentally determined path.

21. Control method according to claim 13, wherein the reference values are discrete points corresponding to the instants of fabrication of the thin layers with respect to the time $t_0$.

22. Control method according to claim 13, wherein the path traveled is adjusted by a polynomial of order between 1 and 5.

23. Control method according to claim 13, wherein the reference values are determined by measurement, using the succession of the following steps:

measurement of a known layer on a simple substrate;

measurement of the same known layer on an industrial substrate;

measurement of the thin-film structure to be controlled.

24. Control method according to claim 1, wherein the ellipsometric measurement is one with phase modulation.

25. A method according to claim 24, wherein the measured control variables are, respectively:

$I_s = (\sin 2\Psi \sin \Delta)$ and $I_c = (\sin 2\Psi \cos \Delta)$ or $I_c = \cos 2\Psi$.

26. Control method according to claim 1, wherein the ellipsometric measurement is carried out using the "rotating polarizer" method.

27. Control method according to claim 26, wherein the measured variables are tan $\Psi$ and cos $\Delta$.

28. Control method according to claim 1, wherein the ellipsometric measurement is a multiwavelength measurement.

29. Control method according to claim 1, wherein the reference values form a theoretically determined path.

30. Control method according to claim 1, wherein the reference values form an experimentally determined path.

31. Control method according to claim 1, wherein the reference values are discrete points corresponding to the instants of fabrication of the thin layers with respect to the time $t_0$.

32. Control method according to claim 1, wherein the path traveled is adjusted by a polynomial of order between 1 and 5.

33. Control method according to claim 1, wherein the reference values are determined by measurement, using the succession of the following steps:

measurement of a known layer on a simple substrate;

measurement of the same known layer on an industrial substrate;

measurement of the thin-film structure to be controlled.

* * * * *